(12) United States Patent
Fiorella

(10) Patent No.: US 8,998,807 B2
(45) Date of Patent: Apr. 7, 2015

(54) RETRACTOR EXTENSIONS AND METHODS OF USE

(75) Inventor: David L. Fiorella, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 261 days.

(21) Appl. No.: 13/279,615

(22) Filed: Oct. 24, 2011

(65) Prior Publication Data

US 2013/0102850 A1 Apr. 25, 2013

(51) Int. Cl.
*A61B 17/02* (2006.01)
*A61B 1/32* (2006.01)
*A61B 1/04* (2006.01)

(52) U.S. Cl.
CPC ... *A61B 1/32* (2013.01); *A61B 1/04* (2013.01); *A61B 17/02* (2013.01)

(58) Field of Classification Search
CPC .................................. A61B 17/02; A61B 1/32
USPC .................................................. 600/201–249
See application file for complete search history.

(56) References Cited

U.S. PATENT DOCUMENTS

| | | | | |
|---|---|---|---|---|
| 5,280,782 | A * | 1/1994 | Wilk | 600/214 |
| 5,512,038 | A | 4/1996 | ONeal et al. | |
| 5,785,647 | A | 7/1998 | Tomkins et al. | |
| 5,984,865 | A | 11/1999 | Farley | |
| 6,042,540 | A * | 3/2000 | Johnston et al. | 600/213 |
| 7,220,228 | B2 | 5/2007 | Hu | |
| 7,455,639 | B2 | 11/2008 | Ritland | |
| 7,491,168 | B2 | 2/2009 | Raymond et al. | |
| 7,833,224 | B2 * | 11/2010 | Schmucki et al. | 606/57 |
| 7,850,608 | B2 | 12/2010 | Hamada | |
| 7,946,982 | B2 | 5/2011 | Hamada | |
| 7,976,463 | B2 | 7/2011 | Dewey et al. | |
| 2002/0147387 | A1 | 10/2002 | Paolitto et al. | |
| 2006/0235279 | A1 | 10/2006 | Hawkes et al. | |
| 2006/0287584 | A1 | 12/2006 | Garcia-Bengochia | |
| 2007/0213722 | A1 * | 9/2007 | Jones et al. | 606/61 |
| 2008/0021285 | A1 | 1/2008 | Drzyzga et al. | |
| 2008/0262318 | A1 | 10/2008 | Gorek et al. | |
| 2009/0187194 | A1 | 7/2009 | Hamada | |
| 2009/0222083 | A1 * | 9/2009 | Nguyen et al. | 623/2.11 |
| 2009/0234395 | A1 * | 9/2009 | Hoffman et al. | 606/86 A |
| 2010/0121153 | A1 | 5/2010 | To | |

OTHER PUBLICATIONS

Aesculap Spine, Caspar Lumbar Retractor System, BRAUN, Tuttlingen, Germany http://www.rafi.ro/fisiere_produse/64.pdf—Website visited Oct. 21, 2011.
The Iowa Orthopaedic Journal, 2003, vol. 23 http://uiortho.com/ioj/2003/Ortho-2003.pdf.
Spine Frontier, Sagittal Lumbar Interbody Fusion Technology, Technique Sheet http://www.spinefrontier.com/resources/slif_sheet.pdf—Website visited Oct. 21, 2011.

* cited by examiner

*Primary Examiner* — Jerry Cumberledge
*Assistant Examiner* — Nicholas Plionis
(74) *Attorney, Agent, or Firm* — Sorell, Lenna & Schmidt LLP

(57) ABSTRACT

A retractor extension is provided comprising a body having a distal end and a proximal end extending longitudinally from the distal end, the distal end of the body comprising a first set of engagement members comprising a first projection configured for attaching the body to a first end surface of the retractor, the proximal end of the body comprising a second set of engagement members comprising a second projection configured for attaching the body to a second end surface of the retractor. In some embodiments, the retractor extension holds tissue away from the surgical incision to enhance the surgeon's field of vision. Methods of attaching the retractor extension to the retractor are also described.

18 Claims, 5 Drawing Sheets

RETRACTOR EXTENSIONS AND METHODS OF USE

TECHNICAL FIELD

The present disclosure generally relates to an extension for a retractor that reduces or prevents tissue encroachment into the surgical incision site.

BACKGROUND

In surgical procedures trauma to the patient and damage to the tissue needs to be minimized as much as possible. To achieve this result, surgeons try to keep incisions as small as possible when performing surgical procedures. This is particularly so when the surgical incision is in the spinal area. However, it is often necessary that the surgeon performing the delicate surgery have a clear view of the operating field. A variety of retractors are available to keep an incision open and provide a clear field of view of the operation.

Typically, the retractor is inserted in the incision to hold organs, muscles, arteries and other tissue out of the way and provide a clear view of the surgical site being operated on. The retractor displaces a small volume of tissue when inserted into the incision before it is opened, or "spread" to provide a clear view of the operating field.

However, a common problem with retractors is that tissue often encroaches in the surgical site and obstructs the surgeons' operating field. For example, in the case of spinal surgery, the bony geometry, which a retractor is intended to expose, is often of an irregular shape, and, sometimes, tissue can creep under the retractor's blades, obscuring vision and blocking the surgical site. This may lead to post-operative wound complications or unwanted damage to tissue.

Sometimes, if there is tissue encroachment into the surgical site, the surgeon will cut or ablate the tissue entering into the surgical site, which can cause further trauma to the patient and delay the operation and postoperative recovery. Therefore, there is a need for a retractor extension that can be attached to a variety of retractors. Retractor extensions and methods that provide a clear field of view of the surgical site by moving tissue away from the surgical site are needed.

SUMMARY

Retractor extensions are provided that can be easily attached to a variety of retractors. These retractor extensions and methods provide a clear field of view of the surgical site by moving tissue away from the surgical site.

In one embodiment, there is a retractor extension comprising a body having a distal end and a proximal end extending longitudinally from the distal end, the distal end of the body comprising a first set of engagement members comprising a first projection configured for attaching the body to a first end surface of the retractor, the proximal end of the body comprising a second set of engagement members comprising a second projection configured for attaching the body to a second end surface of the retractor.

In another embodiment, there is a retractor extension comprising a body having a distal end and a proximal end extending longitudinally from the distal end, the distal end of the body comprising a first set of engagement members comprising a latch and rod movable in a closed position and configured for attaching the body to a first end surface of the retractor, the proximal end of the body comprising a second set of engagement members comprising a second projection configured for attaching the body to a second end surface of the retractor.

In yet another embodiment, there is a method for securing an extension to a retractor, the method comprising attaching a first set of engagement members of an extension to a first end surface of the retractor, the first set of engagement members comprising a projection configured to receive the first end surface of the retractor; attaching a second set of engagement members of the extension to a second end surface of the retractor, the second set of engagement members comprising a latch and rod, the latch movable in a closed position radially over at least a portion of the rod; and moving the latch radially to a closed position to secure the extension to the retractor.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
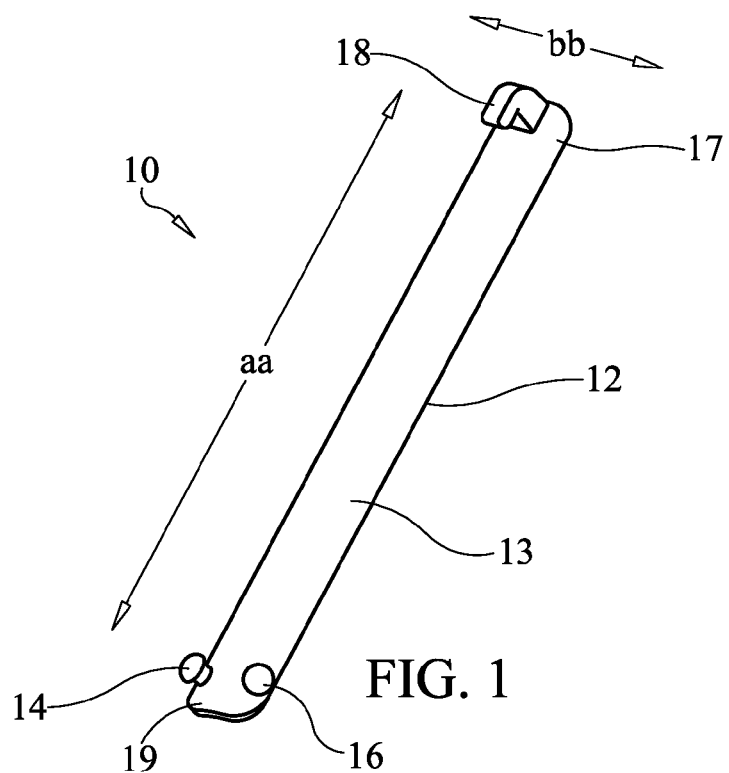
FIG. 1 illustrates a side view of an embodiment of a retractor extension comprising first and second sets of engagement members for attaching the extension to a retractor.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a projection" includes one, two, three or more projections.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The exemplary embodiments of the retractor extension and related methods of use disclosed are discussed in terms of medical devices for the treatment of various conditions, for example, musculoskeletal disorders including spinal disorders. It is envisioned that the retractor extension and methods of use disclosed can be employed in procedures to obtain a posterolateral fusion through a minimally invasive or percutaneous technique. It is further envisioned that the disclosed retractor extension and methods can be used in connection with and/or to supplement an instrumented minimally invasive or percutaneous interbody fusion. In some embodiments, the disclosed retractor extension and methods can be used in a simple decompression procedure, which would not require implantation of any hardware but using a tubular style retractor (e.g., a MetRx® tube retractor), where the retractor extension can be coupled to the tubular retractor.

In one embodiment, one or all of the components of the retractor extension are disposable, peel-pack, pre-packed sterile devices. In some embodiments, the device may be reusable. The retractor extension may be configured as a kit with multiple sized and configured components.

It is envisioned that the disclosed retractor extension may be employed in instrumentation to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed retractor extension and methods may be alternatively employed in a surgical treatment with a patient in a prone or supine position, and/or employ various surgical approaches to the spine, including anterior, posterior, posterior mid-line, postero-lateral, and/or antero-lateral approaches, and in other body regions. The present disclosure may also be alternatively employed with procedures for treating the lumbar, cervical, thoracic and pelvic regions of a spinal column. The retractor extension and methods of the present disclosure may also be used on animals, bone models and other non-living substrates, such as, for example, in training, testing and demonstration.

Retractors are designed in many shapes and sizes for retaining a portal through which a surgical procedure may be performed. In spinal surgery, the bony geometry, which a retractor is intended to expose, is often of an irregular shape, making it difficult to design retractor blades, which adapt to the local anatomy and prevent any tissue encroachment. Often times when a spinal retractor is placed and opened, tissue can creep under the edges of the retractor (e.g. retractor blade), obscuring vision and blocking the surgical site. The present retractor extension can help sweep tissue (e.g., muscles, ligaments, organs, spinal tissue, etc.) away from the surgical site and provide a clear field of view of the surgical site. In some embodiments, the retractor extensions can be attached to a variety of retractors. In some embodiments, the disclosed retractor extension and methods can be used in conjunction with a tubular style retractor (e.g., a MetRx® tube retractor) that do not open any more than their insertion size. In some embodiments, the retractor extension can be placed by hand without need for modifying the retractor blades or use of additional instrumentation.

The following discussion includes a description of a retractor extension and related methods of employing the retractor extension in accordance with the principles of the present disclosure. Alternate embodiments are also disclosed. Reference will now be made in detail to the exemplary embodiments of the present disclosure, which is illustrated in the accompanying figures. Turning now to FIGS. 1-10, there is illustrated components of a retractor extension in accordance with the principles of the present disclosure.

FIG. 1 illustrates a side view of an embodiment of a retractor extension comprising first and second sets of engagement members for attaching the extension to a retractor. More particularly, FIG. 1 illustrates an embodiment of the retractor extension 10 comprising a body 12 having a distal end 17 and a proximal end 19 extending longitudinally (shown as axis aa) from the distal end to the proximal end, the distal end of the body comprising a first set of engagement members, which comprises a first projection 18 configured for attaching the body to a first end surface of the retractor (not shown), the proximal end 19 of the body comprises a second set of engagement members, which comprises a second projection shown as two projections, 14 and 16 configured, for attaching the body to a second end surface of the retractor. The two projections, 14 and 16 are positioned along a transverse axis bb of the body 12.

The components of retractor extension 10 can be fabricated from biologically acceptable materials suitable for medical applications, including metals, synthetic polymers, ceramics, or other materials depending on the particular application and/or preference of a medical practitioner. For example, the components of retractor 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, or combinations thereof. Various components of the retractor extension 10 may have material, including the above materials, to achieve various desired characteristics such as strength, rigidity, elasticity, compliance, biomechanical performance, and/or durability. The components of the retractor extension 10, individually or collectively, may also be fabricated from a heterogeneous material such as a combination of two or more of the above-described materials. The components of retractor extension may be monolithically formed, integrally connected or include fastening elements and/or instruments, as described herein. In some embodiments, the retractor extension 10 or portions thereof may be made from radio-opaque materials. In some embodiments, the retractor extension 10 or portions thereof may be made from radiolucent materials.

In some embodiments, the retractor extension 10 may be made from materials, such as for example, polyurethane, polyurea, polyether(amide), PEBA, thermoplastic elastomeric copolyester, and styrenic thermoplastic elastomer, steel, aluminum, stainless steel, nitinol, titanium, metal alloys with high non-ferrous metal content and a low relative proportion of iron, carbon fiber, glass fiber, plastics, ceramics or combinations thereof.

The retractor extension body 12, in some embodiments, can conform to the geometric size and configuration of the retractor. For example, the retractor extension body can have a smooth or even outer surface 13 and a cylindrical cross-section. It is envisioned that all or only a portion of the outer surface 13 of body 12 may have alternate surface configurations, such as, for example, rough, arcuate, undulating, porous, semi-porous, crescent, dimpled, polished and/or textured according to the requirements of a particular application. It is contemplated that body 12 may have alternate cross section configurations, such as, for example, oval, oblong, triangular, rectangular, square, polygonal, irregular, tubular, non-tubular, uniform, non-uniform, variable and/or tapered. In one embodiment, the retractor extension is complementary in shape to the retractor (e.g., a portion of the retractor is concave and the retractor extension is convex and fits within the retractor).

In some embodiments, the retractor extension can retract tissue that encroaches on the surgical site by from about 2 mm to about 20 mm in one or more directions away from the field of view. In some embodiments, the retractor extension can retract tissue that encroaches on the surgical site by from about 10 mm to about 15 mm in one or more directions away from the field of view.

In some embodiments, the shape and length of the retractor extension can be adapted specifically for different anatomical location where it is to be used (posterior vs. lateral areas). In some embodiments, the retractor extension can be about 5 mm to about 10 mm wide (edge to edge) and extend between about 5 mm to about 10 mm below the bottom (proximal) edge of the retractor. In some embodiments, the retractor is from about 0.5 mm to about 2 mm thick. In some embodiments, the retraction extension comprises a geometric configuration to evenly distribute pressure on the retracted tissue plane without causing excessive tissue damage. For example, the retractor extension can be angled relative to the surgical incision and have a surface area configured to move the tissue away from the surgical incision. In some embodiments, the retractor extension is pliant and will conform to the anatomic region of the surgical incision. In this way, the retractor extension provides a clear field of view of the surgical site for the surgeon to operate.

Shown in FIG. 1 are second set of engagement members comprising at least two projections 14 and 16 at the proximal end 19 of the extension body 12. The projections 14 and 16 are pliant and engage the retractor and bias against an end surface of the retractor. These projections can be disposed in or on the retractor at discrete positions. Although the projections 14 and 16 are shown as raised circular projections relative to the surface of the retractor extension, it will be understood that the projections can be any shape including, oval, oblong, triangular, rectangular, square, polygonal, irregular, tubular, non-tubular, uniform, non-uniform, variable and/or tapered in shape. In some embodiments, the projection comprises a loop, hook, barb, post, tab, latch, prong and/or clip in or on the distal or proximal end of the body.

Shown in FIG. 1 at the distal end 17, there is a set of first projections 18 shown as a hook. The hook is configured to receive an end surface of the retractor. On application of force perpendicular to the retractor, the retractor extension is aligned with and attached to the retractor. For example, the distal end 17 can be hooked onto the retractor and then the projections 14 and 16 at the proximal end can be pressed onto the retractor over its edge. The retractor extension 10 will engage and align with the retractor (e.g., snap on, force fit, press fit, etc) to provide a snug and taut connection to the retractor. For example, the projections can be configured so that force can be applied by hand or machine to the extension in the direction toward the retractor to attach the extension to the retractor. In some embodiments, the projections are configured for "slip and snap" or "slide and snap" fitting to one or more surfaces of the retractor. Although a hook is shown as the projection at distal end 17, it will be understood that the projection can be a loop, barb, post, tab, latch, prong, and/or clip in or on the distal end of the body. This configuration allows the extension to be universally adapted to various shapes, sizes, and/or geometries of the retractor. In some embodiments, the retractor extension body is the same thickness or less thick than the retractor. In some embodiments, the retractor body has a uniform thickness. In some embodiments, the retractor body has portions that have different thicknesses that are less thick than the retractor.

In some embodiments, the retractor extension is single use and disposable. In some embodiments, the extension can be reusable. For example, after use, in some embodiments, the retractor extension can be detachable from the retractor by moving the retractor extension in a direction away from the retractor, to dislodge it, and each part of the retractor extension can be cleaned and sterilized for re-use.

In some embodiments, in the method of using the retractor extension, a surgeon can employ a minimally invasive technique and make an incision in the skin of a patient over and in approximate alignment with a surgical site. The retractor then can be used and includes the retractor extension 10 of FIG. 1 employed to separate the muscles and tissues to create a passageway along a desired trajectory to the surgical site through which the surgery may be performed. It is contemplated that the retractor extension gradually separates muscle and tissue to create a portal including the passageway. It is further contemplated that the retractor extension may be configured to be used with an in-situ guidance instrument and may include an endoscope camera tip. In some embodiments, the retractor extension 10 is attached to a retractor (not shown), which is positioned and docked adjacent to the surgical site over the incision.

In some embodiments, the retractor extension 10 can be placed before the retractor or blade (not shown) is inserted into the incision or after the retractor or blade is already placed in the incision. It is contemplated that retractor extension 10 of different lengths may be used on different blades or different sides or surface of the retractor based on conditions encountered by the surgeon.

Figure 2:
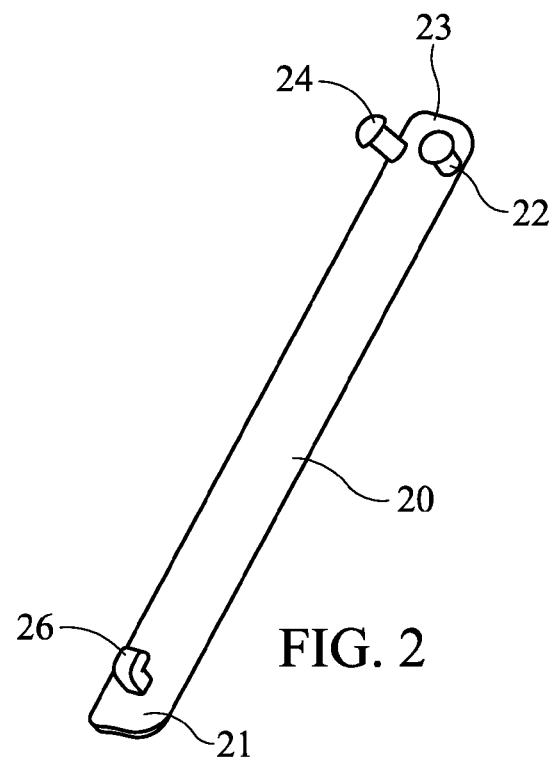
FIG. 2 illustrates a side view of an embodiment of a retractor extension comprising first and second sets of engagement members for attaching the extension to a retractor.

FIG. 2 illustrates a side view of an embodiment of a retractor extension comprising first and second sets of engagement members for attaching the extension to a retractor. More particularly, FIG. 2 illustrates an embodiment of the retractor extension comprising a body 20 having a distal end 23 and a proximal end 21 extending longitudinally from the distal end to the proximal end, the distal end of the body comprising a first set of engagement members, which comprises first projections 24 and 22 configured for attaching the body to a first end surface of the retractor (not shown), the proximal end 21 of the body comprising a second set of engagement members, which comprises a second projection shown as a hook 26.

The hook is configured to receive an end surface of the retractor. On application of force perpendicular to the retractor, the retractor extension is aligned with and attached to the retractor. For example, the proximal end 21 can be hooked onto the retractor and then the projections 22 and 24 at the distal end can be pressed onto gaps of the retractor. The hook can, in some embodiments, be rigid and inflexible or static. In some embodiments, the projections 22 and 24 can be flexible and by applying pressure on the extension, the retractor extension will engage and align with the retractor (e.g., snap on, force fit, press fit, etc.) to provide a snug and taut connection to the retractor. For example, the projections can be configured so that force can be applied by hand or machine to the extension in the direction toward the retractor to attach the extension to the retractor. In some embodiments, the engagement members can be flexible or rigid or a combination thereof for ease of attachment to the retractor or detachment from the retractor. In some embodiments, the first projection (e.g., prongs) is disposed at a position generally center to the second projection (e.g., hook). In some embodiments, all or a portion of the retractor extension is flexible. In some embodiments, all or a portion of the retractor extension is inflexible.

Figure 3:
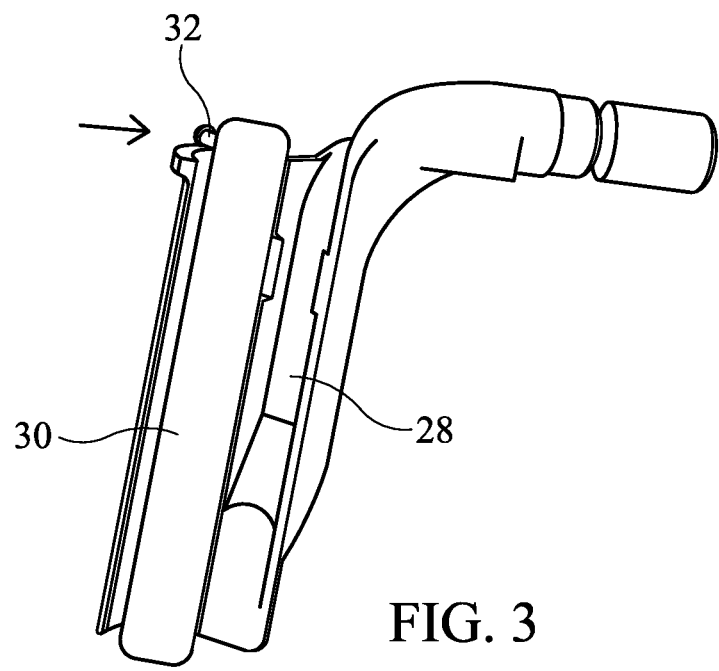
FIG. 3 illustrates a side view of an embodiment of a retractor extension attached to a retractor.

FIG. 3 illustrates a side view of an embodiment of a retractor extension 30 attached to a retractor 28. In the embodiment shown, the distal end of the retractor extension has engagement members (shown as tab 32) attached to the retractor. The retractor extension 30 is shown engaged and aligned with the retractor 28 snap on, force fit, press fit, etc.) to provide a snug connection to the retractor. As the retractor is moved so is the retractor extension as one unit. The retractor extension is detachable so that force applied by hand or machine (shown as the dark arrow) to the extension in the direction away from the retractor can detach the extension from the retractor. In some embodiments, the retractor extension can be continuous with the retractor.

Figure 4:
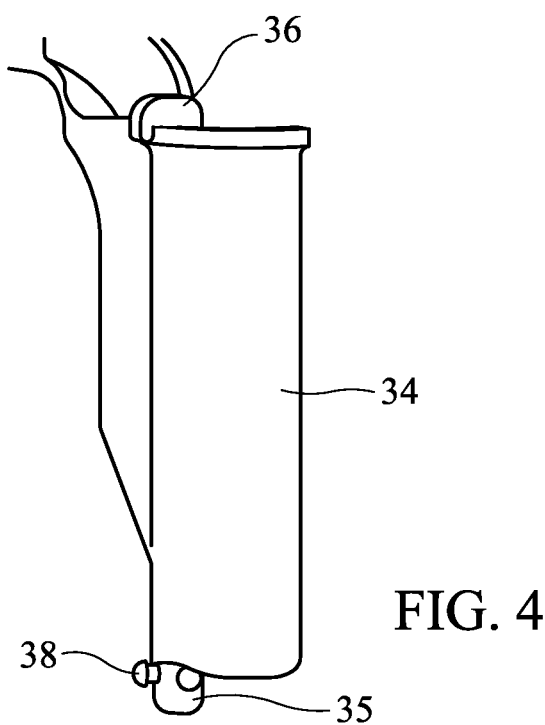
FIG. 4 illustrates a side view of an embodiment of a retractor extension attached to a retractor.

FIG. 4 illustrates a side view of an embodiment of a retractor extension 35 attached to a retractor blade 34. In the embodiment shown, the first engagement member is shown as a static hook 36 that is immovable, while second engagement member comprises a projection 38 that is flexible or movable. On application of force to the extension, the flexible projection will snap into place on the edge of retractor for use. In some embodiments, as shown, the retractor extension 35 has a length that is longer than the retractor and the engagement members (e.g., hook, loop, barb, post, tab, latch, prong, clip, etc.), shown as a hook at 36 extends above the retractor 34 or the projection 38 extends below the retractor 34. In this way, the extension increases the surface area of the retractor and its contact with more tissue, which can prevent tissue from encroaching into the surgical incision, and the retractor extension provides a clear field of view of the surgical site for the surgeon to operate.

In some embodiments, the body of the retractor extension runs longitudinally with and substantially parallel to the retractor as shown in FIG. 4. In some embodiments, the body of the retractor extension comprises a curved surface corresponding to a curved surface of the retractor and allows the retractor extension to mate with the retractor. In some embodiments, the retractor extension comprises surface configurations allowing it to be held in a hand of a user.

Figure 5:
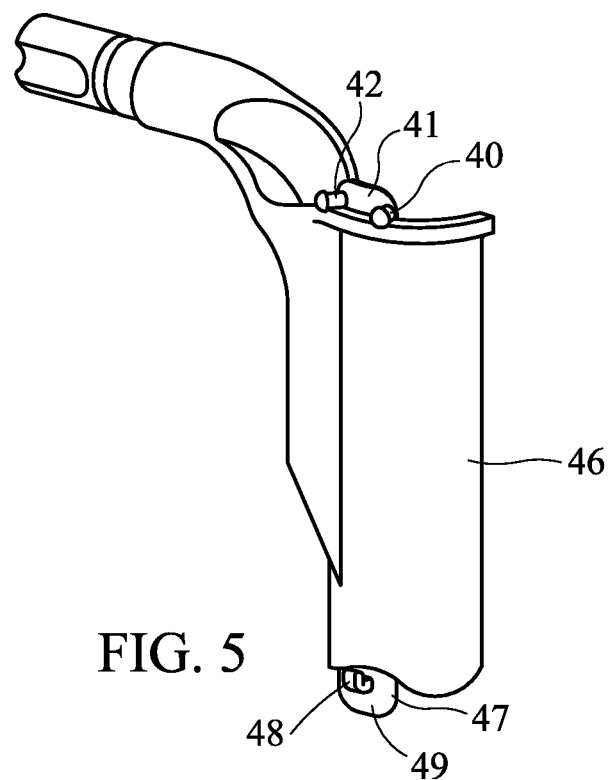
FIG. 5 illustrates a side view of an embodiment of a retractor extension attached to a retractor.

FIG. 5 illustrates a side view of an embodiment of a retractor extension 47 attached to a retractor blade 46. In the embodiment shown, the second engagement member is shown as a static hook 48 that is immovable and disposed at the proximal end 49 of the retractor extension 47, while first engagement member comprises projections 40 and 42 that are flexible or movable and disposed at the distal end 41 of the retractor extension 47. On application of force to the extension, the flexible or movable projection will snap into place over the edge of retractor for use. In some embodiments, as shown, the retractor extension 47 has a length that is longer than the retractor and the engagement members (e.g., hook, loop, barb, post, tab, latch, clip, etc.), shown as a hook at 48, extends below the retractor blade 46 and over its edge or the projections 40 and 42 extend above the retractor blade 46 and over its edge. In this way, the extension increases the surface area of the retractor and its contact with more tissue, which can prevent tissue from encroaching into the surgical incision, and the extension provides a clear field of view of the surgical site for the surgeon to operate.

Figure 6:
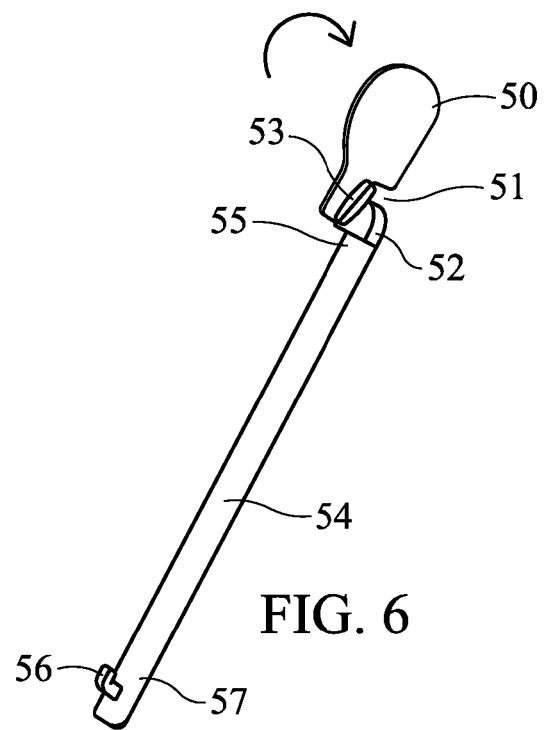
FIG. 6 illustrates a side view of an embodiment of a retractor extension comprising first and second sets of engagement members for attaching the extension to a retractor (the first set of engagement members is shown as a latch in an open position)

FIG. 6 illustrates a side view of an embodiment of a retractor extension comprising first and second sets of engagement members for attaching the extension to a retractor. The first set of engagement members is shown as a latch 50 in the open position.

More particularly, FIG. 6 illustrates an embodiment of the retractor extension comprising a body 54 having a distal end 55 and a proximal end 57 extending longitudinally from the distal end to the proximal end, the distal end of the body comprising a first set of engagement members, which comprises a latch 50 configured for attaching the body to a first end surface of the retractor (not shown). The latch 50 is rotably mounted to the distal end 55 (e.g., rod, pin, etc.) of the retractor extension body 54. The latch can comprise a notch that is configured to be a corresponding reciprocal shape and be received into rest 52 to lock the latch into place when the latch 50 is rotated in a closed position. The latch may have ridge 53 configured to further hold the latch in a closed position and/or provide a further snug or friction fit to keep the latch in a closed position. Here the latch 50 is shown in an open position. The proximal end 57 comprises a second set of engagement members, which comprises a second projection shown as a hook 56. On rotating latch clockwise (shown by a black arrow) or in a downward position shown by the arrow, the latch pulls hook 56 in an upward direction causing tension on the retractor end so as to cause the retractor extension to attach snugly, taut or lock onto the retractor. It will be understood that embodiments can be designed where the latch is rotated counterclockwise to achieve the same locking effect. In some embodiments, the hook and/or latch is made flexible or rigid depending on the design of the retractor extension desired.

Figure 7:
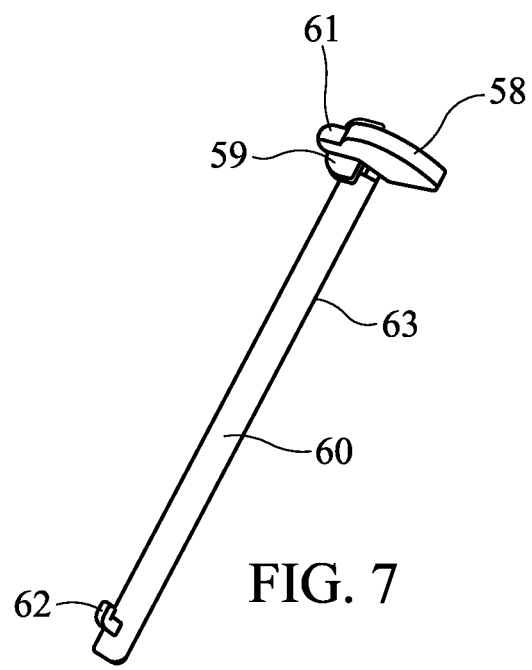
FIG. 7 illustrates a side view of an embodiment of a retractor extension comprising first and second sets of engagement members for attaching the extension to a retractor (the first set of engagement members is shown as a latch in the closed position)

FIG. 7 illustrates a side view of an embodiment of a retractor extension 60 comprising first and second sets of engagement members for attaching the extension to a retractor. The first set of engagement members is shown as a latch 58 in the closed position. More particularly, FIG. 7 illustrates an embodiment of the retractor extension comprising a body 63 having a distal end and a proximal end extending longitudinally from the distal end to the proximal end, the distal end of the body comprising a first set of engagement members, which comprises a latch 58 configured for attaching the body to a first end surface of the retractor (not shown). The latch 58 is rotably mounted to the distal end by rod or pin 61. The latch can comprise a notch that is configured to be a corresponding reciprocal shape and be received into rest 59 to lock the latch into place when the latch 50 is rotated in a closed position (shown). The latch may have a ridge configured to further hold the latch in a closed position and/or provide a further snug or friction fit to keep the latch in a closed position. The proximal end of the retractor extension comprises a second set of engagement members, which comprises a second projection shown as a hook 62. On rotating the latch clockwise, the latch pulls hook 62 in an upward direction causing tension on the retractor end so as to cause the retractor extension to attach snugly or lock onto the retractor.

Figure 8:
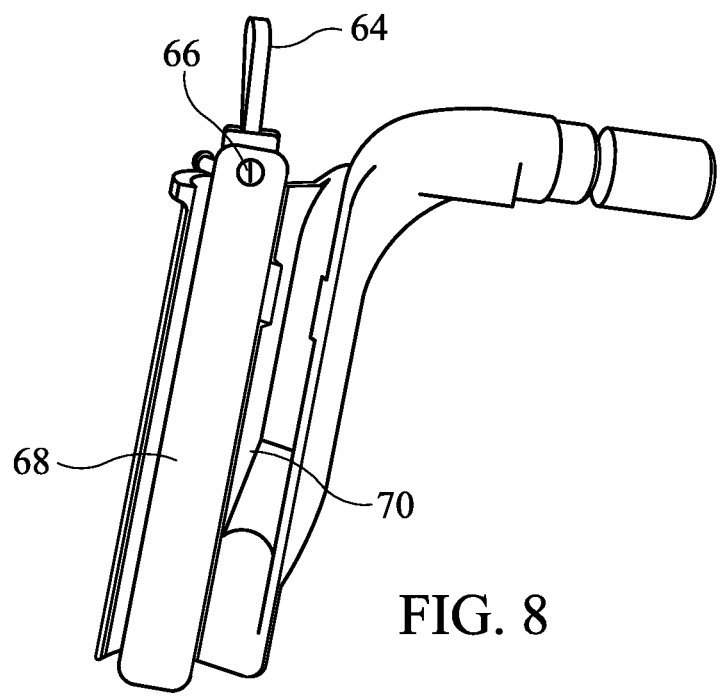
FIG. 8 illustrates a side view of an embodiment of a retractor extension attached to a retractor (the latch is shown in the open position)

FIG. 8 illustrates a side view of an embodiment of a retractor extension 68 comprising first and second sets of engagement members attached to a retractor 70. The first set of engagement members is shown as a latch 64 in the open position. More particularly, FIG. 8 illustrates an embodiment of the retractor extension comprising a first set of engagement members, which comprises a latch 64 attached to a first end surface of the retractor 70. The latch 64 is rotably mounted to the retractor extension by a pin, rod, nail, or screw 66 that allows the latch to rotate counterclockwise or clockwise so that the latch can lock the retractor extension in a closed position on the retractor. On rotating the latch, the latch pulls the projection member in an upward direction causing tension on the retractor end so as to cause the retractor extension to attach snugly or lock onto the retractor.

Figure 9:
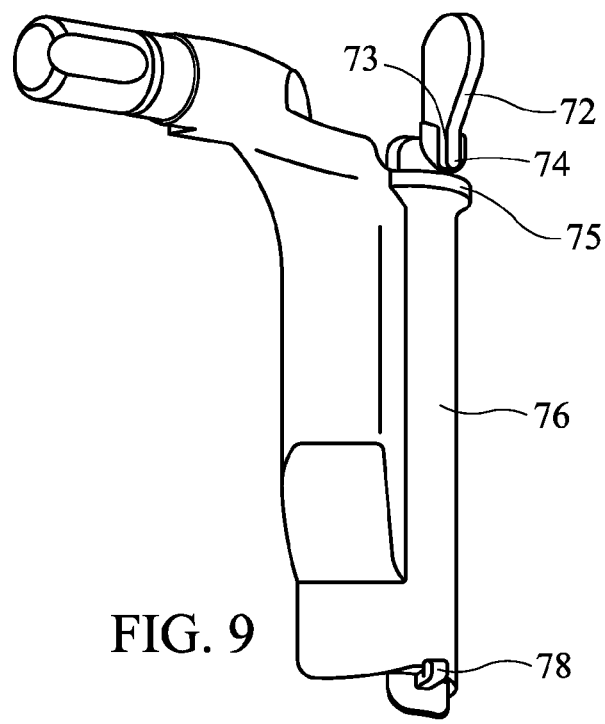
FIG. 9 illustrates a side view of an embodiment of a retractor extension attached to a retractor (the latch is shown in the open position)

FIG. 9 illustrates a side view of an embodiment of a retractor extension comprising first and second sets of engagement members attached to a retractor 76. The first set of engagement members is shown as a latch 72 in the open position. More particularly, FIG. 9 illustrates an embodiment of the retractor extension comprising a first set of engagement members, which comprises a latch 72 attached to a first end surface 75 of the retractor 76. The latch 72 is rotably mounted to the retractor extension by a pin, rod, nail, or screw 74 that allows the latch to rotate counterclockwise or clockwise so that the latch can lock the retractor extension in a closed position on the retractor. On rotating the latch, the latch pulls hook 78 in an upward direction causing tension on the retractor end so as to cause the retractor extension and ridge 73 of the retractor extension to slide snugly or lock onto the retractor end surface 75.

Figure 10:
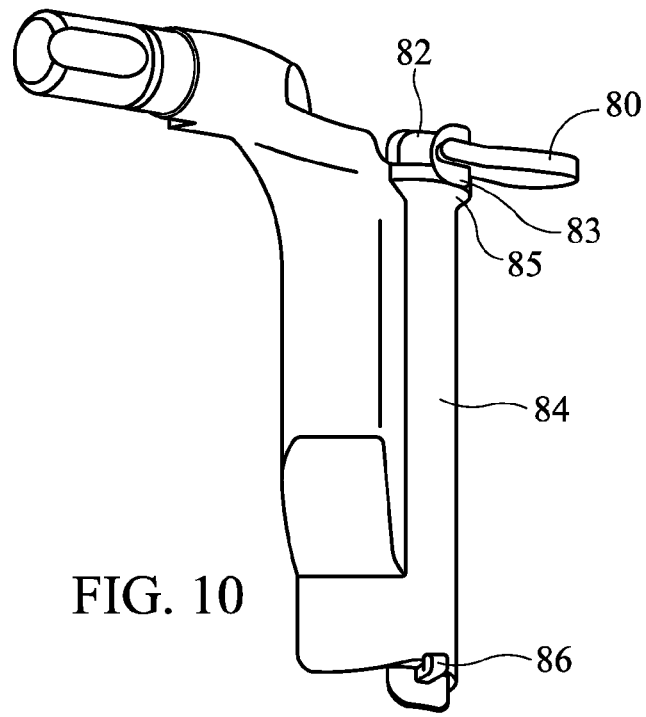
FIG. 10 illustrates a side view of an embodiment of a retractor extension attached to a retractor (the latch is shown in the closed position).

FIG. 10 illustrates a side view of an embodiment of a retractor extension 82 comprising first and second sets of engagement members for attaching the extension to a retractor 84. The first set of engagement members is shown as a latch 80 in the closed position. More particularly, FIG. 10 illustrates an embodiment of the retractor extension comprising a first set of engagement members, which comprises a latch 80 configured for attaching the body to a first end surface of the retractor. The latch 80 is rotably mounted to the distal end of the retractor extension by a rod or pin that allows the latch to rotate counterclockwise or clockwise so that the latch can lock the retractor extension in a closed position on the retractor. On rotating the latch in a downward direction, the latch pulls hook 86 in an upward direction causing tension on the retractor end so as to cause the retractor extension and ridge 83 of the retractor extension to slide snugly or lock onto the retractor edge 85.

In some embodiments, the ridge 83 of the retractor extension can be configured to be spaced a distance from the extension body and allow the edge of the retractor to be received within the space between the extension and the ridge, and on moving the ridge over the retractor, the ridge contacts and secures the retractor edge in a locked position. In some embodiments, the latch is flush with the retractor and slides over it and adjacent to it to lock it onto the edge of the retractor. In some embodiments, and as shown in FIG. 10, the latch 80 is movable in a closed position substantially transverse to the longitudinal axis of the extension body and/or the retractor.

In some embodiments, the retractor extension may comprise indicator markings (e.g., numbers, lines, letters, radiographic markers, color, etc.) disposed on the body, distal and/or proximal end to indicate position, extension of the device and/or length of extension (e.g., 1 mm, 5 mm, 10 mm, etc). In some embodiments, the retractor extension may comprise markings to indicate that it is in the open position or the closed position. In some embodiments, the retractor extension may have contours and allow easy grasping of the device during use. The retractor extension can be angled for right and left hand users or can be generic for both hands. In some embodiments, the retractor extension is transparent so the user can see the position of the retractor extension when it is attached to the retractor.

In some embodiments, the retractor extension can be easily attached to the retractor by snapping the projections onto the edge of the retractor and/or moving the latch. In some embodiments, there is a method for securing an extension to a retractor, the method comprising attaching a first set of engagement members of an extension to a first end surface of the retractor, the first set of engagement members comprising a projection configured to receive the first end surface of the retractor; attaching a second set of engagement members of the extension to a second end surface of the retractor, the second set of engagement members comprising a latch and rod, the latch movable in a closed position radially over the rod; and moving the latch radially to a dosed position to secure the extension to the retractor.

In some embodiments, the retractor extension may be employed for performing spinal surgeries, such as, for example, discectomy, laminectomy, fusion, laminotomy, nerve root retraction, foramenotomy, facetectomy, decompression, spinal nucleus or disc replacement and bone graft and implantable prosthetics including plates, rods, and/or bone engaging fasteners.

In some embodiments, the retractor extension may be lightweight, disposable and sterilizable such that when the device is assembled (e.g., the retractor extension is attached to the retractor), the weight of the device does not substantially increase. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in some embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the device, including, but not limited to, gas sterilization, such as, for example, with ethylene oxide or steam sterilization.

In some embodiments, a kit is provided which may include additional parts along with the retractor extension device combined together to be used to retract tissue. The kit may include the retractor extension device in a first compartment. The second compartment may include the retractor, and any other instruments needed for the surgery. A third compartment may include gloves, drapes, wound dressings and other procedural supplies for maintaining sterility of the retractor and/or retractor extension, as well as an instruction booklet. A fourth compartment may include cannulas and/or needles. Each tool may be separately packaged in a plastic pouch that is radiation sterilized. A cover of the kit may include illustrations of methods of using the retractor extension and a clear plastic cover may be placed over the compartments to maintain sterility.

In some embodiments, a kit is provided, the kit comprising one or more retractor extension devices each having a plurality of lengths and/or widths (such as for example, arc length) to attach to different blade/retractor lengths and/or widths. In some embodiments, different extension lengths and/or widths may be indicated by different indicator markings (e.g., numbers, lines, letters, radiographic markers, color, etc.) disposed on all or a portion of the device (e.g., the body, distal and/or proximal end).

In some embodiments, a kit is provided, the kit comprising one or more retractor extension devices each having a plurality of different lengths to attach to different blade/retractor lengths. In some embodiments, different extension lengths may be indicated by different indicator markings (e.g., numbers, lines, letters, radiographic markers, colors, etc.) disposed on all or a portion of the device (e.g., the body, distal and/or proximal end).

In some embodiments, a kit is provided, the kit comprising one or more retractor extension devices each having a plurality of different widths (such as for example, arc length) to attach to different blade/retractor widths. In some embodiments, different extension widths may be indicated by different indicator markings (e.g., numbers, lines, letters, radiographic markers, colors, etc.) disposed on all or a portion of the device (e.g., the body, distal and/or proximal end).

In some embodiments, a kit is provided, the kit comprising one or more retractor extension devices each having a plurality of both different lengths and widths (such as for example, arc length) to attach to different blade/retractor lengths and widths. In some embodiments, different extension lengths and widths may be indicated by different indicator markings (e.g., numbers, lines, letters, radiographic markers, color, etc.) disposed on all or a portion of the device (e.g., the body, distal and/or proximal end).

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A retractor system comprising:
   a retractor comprising a retractor blade, the retractor blade comprising a first end surface, an opposite second end surface, an inner surface and an opposite outer surface; and
   a retractor extension comprising a body having a first surface and an opposite second surface, the body having a distal end and a proximal end extending longitudinally from the distal end, "the first surface of the retractor extension engages the inner surface of the retractor blade", the distal end of the body comprising a first set of engagement members comprising a latch engaging the first end surface of the retractor, the latch extending from the first surface, the latch comprising a ridge that is spaced apart from the first surface, the proximal end of the body comprising a second set of engagement members comprising a hook engaging the second end surface of the retractor,
   wherein the latch is rotatable relative to the body between a first position in which the ridge is spaced apart from the outer surface and a second position in which the ridge engages the outer surface to fix the retractor extension to the retractor.

2. A retractor system according to claim 1, wherein the latch extends perpendicular to the hook when the latch is in the second position.

3. A retractor system according to claim 1, wherein the hook is flexible.

4. A retractor system according to claim 1, wherein the latch is longitudinally aligned with the hook when the latch is in the first position.

5. A retractor system according to claim 1, wherein the body is configured to prevent tissue from covering a wound.

6. A retractor system according to claim 5, wherein the wound is a spinal surgical site.

7. A retractor system according to claim 1, wherein the latch is flexible.

8. A retractor system according to claim 1, wherein the body includes first and second side surfaces extending between the proximal and distal ends of the body, the second surface of the body having a continuous concave curvature between the first and second side surfaces.

9. A retractor system according to claim 1, wherein the latch is moved from the first position to the second position in either a clockwise direction or counterclockwise direction.

10. A retractor system comprising:
a retractor comprising a retractor blade, the retractor blade comprising a first end surface, an opposite second end surface, an inner surface and an opposite outer surface; and
a retractor extension comprising a body having a first surface and an opposite second surface, the body having a distal end and a proximal end extending longitudinally from the distal end, the first surface of the retractor extension engages the inner surface of the retractor blade, the first, the distal end of the body comprising a first set of engagement members engaging the first end surface of the retractor, the first set of engagement members comprising a latch extending from the first surface, the latch defining a longitudinal axis and comprising a ridge extending transverse to the longitudinal axis along an entire length of the ridge, the ridge being spaced apart from the first surface, the proximal end of the body comprising a second set of engagement members comprising a flexible second projection engaging the second end surface of the retractor,
wherein the latch that is rotatable relative to the body between a first position in which the ridge is spaced apart from the outer surface and a second position in which the ridge engages the outer surface to fix the retractor extension to the retractor.

11. A retractor system according to claim 10, wherein the latch comprises a notch configured to receive the first end surface of the retractor.

12. A retractor system according to claim 10, wherein the longitudinal axis of the latch is substantially transverse to a longitudinal axis defined by the body when the latch is in the second position.

13. A retractor system according to claim 10, wherein the latch and/or body comprises markers that indicate the second position.

14. A retractor system according to claim 10, wherein the latch is rotatably mounted to the retractor extension by a rod and the rod extends perpendicular to a longitudinal axis defined by the body.

15. A retractor system according to claim 10, wherein the latch is rotatably mounted to the retractor extension by a rod and the rod is a screw.

16. A method for securing an extension to a retractor, the method comprising:
providing the retractor system recited in claim 1;
attaching the first set of engagement members of the retractor extension to the first end surface of the retractor such that the latch engages the first end surface of the retractor;
attaching the second set of engagement members of the retractor extension to the second end surface of the retractor such that the hook engages the second end surface of the retractor; and
moving the latch radially to a closed position to secure the retractor extension to the retractor.

17. A method according to claim 16, wherein the retractor extension prevents tissue from covering a wound.

18. A method according to claim 16, wherein the latch comprises a marker for indicating the second position of the latch.

* * * * *